(12) United States Patent
Flach et al.

(10) Patent No.: US 11,331,406 B2
(45) Date of Patent: May 17, 2022

(54) MEDICAL DRESSING (71) Applicant: Mölnlycke Health Care AB, Gothenburg (SE)

(72) Inventors: Niclas Flach, Alingsås (SE); Kristina Hamberg, Gothenburg (SE); Ulf Johannison, Landvetter (SE); Bengt Söderström, Mölnlycke (SE)

(73) Assignee: MÖLNLYCKE HEALTH CARE AB, Gothenburg (SE)

( * ) Notice: Subject to any disclaimer, the term of this patent is extended or adjusted under 35 U.S.C. 154(b) by 337 days.

(21) Appl. No.: 15/509,029

(22) PCT Filed: Sep. 9, 2015

(86) PCT No.: PCT/EP2015/070648
§ 371 (c)(1),
(2) Date: Mar. 6, 2017

(87) PCT Pub. No.: WO2016/038109
PCT Pub. Date: Mar. 17, 2016

(65) Prior Publication Data
US 2017/0258956 A1    Sep. 14, 2017

(30) Foreign Application Priority Data
Sep. 11, 2014    (EP) .................................... 14184431

(51) Int. Cl.
*A61L 15/58*    (2006.01)
*A61L 15/26*    (2006.01)
(Continued)

(52) U.S. Cl.
CPC ........ *A61L 15/58* (2013.01); *A61F 13/00063* (2013.01); *A61F 13/023* (2013.01);
(Continued)

(58) Field of Classification Search
CPC .......... A61L 2300/104; A61L 26/0066; A61L 15/44; A61L 26/00; A61L 26/0095;
(Continued)

(56) References Cited

U.S. PATENT DOCUMENTS

| | | |
|---|---|---|
| 4,643,180 A | 2/1987 | Feld |
| 4,921,704 A | 5/1990 | Fabo |

(Continued)

FOREIGN PATENT DOCUMENTS

| | | | |
|---|---|---|---|
| CN | 1925819 A | 3/2007 | |
| EP | 0255248 A2 * | 2/1988 | ............. A61L 15/46 |

(Continued)

OTHER PUBLICATIONS

International Preliminary Report on Patentability dated Mar. 14, 2017 by the International Searching Authority for Application No. PCT/EP2015/070648, which was filed on Sep. 9, 2015 and published as WO/2016/038109 on Mar. 17, 2016 (Applicant—Mölnlycke Health Care AB // Inventors—Flach, et al.) (8 pages).

(Continued)

*Primary Examiner* — Caitlin A Carreiro
(74) *Attorney, Agent, or Firm* — Ballard Spahr LLP (57) ABSTRACT

A medical dressing is described having a substrate with a first chemical compound, said substrate having a first surface, wherein said medical dressing further includes an adhesive layer having a skin-facing surface to adhere said medical dressing to a dermal surface, wherein at least a portion of said skin-facing surface has a coating with a second chemical compound. Also described is a method of manufacturing such a medical dressing.

11 Claims, 3 Drawing Sheets

(51) Int. Cl.
| | |
|---|---|
| *A61L 15/44* | (2006.01) |
| *A61L 15/46* | (2006.01) |
| *A61F 13/00* | (2006.01) |
| *A61F 13/02* | (2006.01) |
| *A61L 15/18* | (2006.01) |
| *A61L 15/42* | (2006.01) |

(52) U.S. Cl.
CPC ...... *A61F 13/0206* (2013.01); *A61F 13/0213* (2013.01); *A61F 13/0253* (2013.01); *A61L 15/18* (2013.01); *A61L 15/26* (2013.01); *A61L 15/425* (2013.01); *A61L 15/44* (2013.01); *A61L 15/46* (2013.01); *A61L 2300/104* (2013.01); *A61L 2300/404* (2013.01); *A61L 2420/08* (2013.01); *C08G 2110/0008* (2021.01)

(58) Field of Classification Search
CPC .......... A61L 15/00; A61L 15/58; A61L 15/16; A61L 15/18; A61L 15/20; A61L 15/585; A61L 2300/00; A61L 2300/10; A61L 2300/102; A61L 2300/404; A61F 13/00063; A61F 13/8405; A61F 2013/0071; A61F 2013/00089; A61F 2013/00719; A61F 2013/00561; A61F 2013/00655; A61F 2013/00646; A61F 13/00; A61F 13/00008; A61F 13/00021; A61F 13/023; A61F 13/0266; A61F 13/00085; A61F 13/0243; A61F 13/0246; A61F 13/0253; A61F 13/02; B01J 20/28026; B01J 20/28016; B01J 20/28019; Y10T 428/25; B32B 2305/54; B32B 25/02; A61K 33/38; A61K 9/16; A61K 9/70; A61K 9/7007; A61K 9/7015; A61K 9/50; A61K 9/2081; A61K 9/2077; A61K 9/51
USPC .... 424/618, 443–448, 469, 489; 602/47, 48, 602/54, 41–46, 52, 57, 58; 523/122; 604/304, 307; 428/321.5, 323, 320.2, 402
See application file for complete search history.

(56) References Cited

U.S. PATENT DOCUMENTS

| | | |
|---|---|---|
| 2006/0141015 A1 | 6/2006 | Tessier et al. |
| 2006/0211965 A1* | 9/2006 | Horn ............... A61L 15/18 602/13 |
| 2007/0203442 A1 | 8/2007 | Bechert et al. |
| 2007/0207186 A1* | 9/2007 | Scanlon ............ A61F 2/91 424/424 |
| 2009/0104252 A1 | 4/2009 | Alam et al. |
| 2010/0021514 A1* | 1/2010 | Fugmann ......... A01N 25/10 424/409 |
| 2012/0089068 A1* | 4/2012 | Mcclure, Jr. ..... A61F 13/00029 602/48 |
| 2013/0101633 A1 | 4/2013 | Lowenhielm et al. |
| 2013/0189339 A1 | 7/2013 | Vachon |
| 2017/0258956 A1 | 9/2017 | Flach et al. |

FOREIGN PATENT DOCUMENTS

| | | | |
|---|---|---|---|
| EP | 1960164 A1 | 8/2008 | |
| EP | 1964580 A1 | 9/2008 | |
| EP | 2 433 594 | 3/2012 | |
| EP | 2837370 A1 | 2/2015 | |
| JP | 2007517557 A | 7/2007 | |
| JP | 2008-509741 | 4/2008 | |
| JP | 2009-518124 | 5/2009 | |
| WO | WO-97/042985 A1 | 11/1997 | |
| WO | WO 2006/020708 | 2/2006 | |
| WO | WO 2006/020708 A2 | 2/2006 | |
| WO | WO 2007/011612 A2 | 1/2007 | |
| WO | WO 2007/067535 | 6/2007 | |
| WO | WO-2007/069990 A1 | 6/2007 | |
| WO | WO-2008/057155 A1 | 5/2008 | |
| WO | WO-2009/047564 A2 | 4/2009 | |
| WO | WO-2009047564 A2 * | 4/2009 | ............ A61L 15/52 |
| WO | WO 2010/122665 | 10/2010 | |
| WO | WO-2011/007179 A1 | 1/2011 | |
| WO | WO-2011/129759 A1 | 10/2011 | |
| WO | WO-2013/128606 A1 | 9/2013 | |
| WO | WO-2016/038111 A1 | 3/2016 | |

OTHER PUBLICATIONS

International Search Report and Written Opinion dated Nov. 18, 2015 by the International Searching Authority for Application No. PCT/EP2015/070650, which was filed on Sep. 9, 2015 and published as WO/2016/038111 on Mar. 17, 2016 (Applicant—Mölnlycke Health Care AB // Inventors—Flach, et al.) (9 pages).
International Preliminary Report on Patentability dated Mar. 14, 2017 by the International Searching Authority for Application No. PCT/EP2015/070650, which was filed on Sep. 9, 2015 and published as WO/2016/038111 on Mar. 17, 2016 (Applicant—Mölnlycke Health Care AB // Inventors—Flach, et al.) (6 pages).
International Search Report and Written Opinion dated Nov. 12, 2015 by the International Searching Authority for Application No. PCT/EP2015/070648, which was filed on Sep. 9, 2015 and published as WO/2016/038109 on Mar. 17, 2016 (Applicant—Mölnlycke Health Care AB // Inventors—Flach, et al.) (11 pages).
U.S. Appl. No. 15/509,111, filed Sep. 9, 2015, Niclas Flach.
PCT, PCT/EP2015/070650 (WO/2016/038111), Sep 9, 2015 (Mar. 17, 2016), Mölnlycke Health Care AB
Davoudi, Zahra Mohammad et al. "Hybrid Antibacterial Fabrics with Extremely High Aspect Ratio Ag/AgTCNQ Nanowires", Advanced Functional Materials (2014), 24, pp. 1047-1053.
Matsumura, Hajime, Japanese Journal of Plastic Surgery (2012), vol. 55, extra issue, pp. S268-S274.

* cited by examiner

MEDICAL DRESSING

CROSS-REFERENCE TO RELATED APPLICATIONS

This application is a U.S. National Phase Application of International Application No. PCT/EP2015/070648, filed Sep. 9, 2015, which claims priority to European Application No. 14184431.6, filed Sep. 11, 2014, each of which are hereby incorporated by reference in their entirety.

FIELD OF INVENTION

The present invention relates to a medical dressing.

BACKGROUND OF THE INVENTION

A wound caused by an injury or disease may be treated by the use of a bandage or wound dressing to promote healing by preventing infection and leakage from the wound. Many known wound dressings include a self-adhering adhesive, also known as pressure-sensitive adhesive (PSA), which purpose is to adhere to the wound and/or to the skin surrounding the wound and thus to fixate the dressing in a desirable position. Various adhesives are being used for affixing medical products on the skin, some of the most common being encompassed by the terms acrylic adhesives, silicone based adhesives and hot melt adhesives, among others.

In order to ensure that a medical device such as a wound dressing remains in the same position after a certain time of use, an adhesive having a strong adherence, e.g. an acrylic adhesive, may be used. However, in case the medical device is to be attached directly on the skin, an acrylic based adhesive increases the risk for pain and damages to the skin when such medical device is to be removed from the skin, e.g. due to skin stripping.

In contrast to acrylic adhesives, silicone based adhesives are known in the art to be very gentle on the skin. This is because a silicone based adhesive is typically relatively soft and therefore it can follow the contours of the skin well, resulting in a large contact surface area between the adhesive and the skin. Thus, although the actual adhesive force in each contact point of a silicone based adhesive is less than that of an acrylic adhesive, the large contact surface area achieved with a silicone based adhesive affords a high overall adherence to the skin, whilst at the same time being skin-friendly, i.e. when a silicone based adhesive is removed from the skin very few skin cells are removed due to the low adhesive force in each contact point, thereby the above mentioned problem of skin stripping can be avoided.

For some type of wounds, such as for example severe burns and chronic wounds, there is a particular need to use a wound dressing that includes an antimicrobial agent to thereby eliminate or reduce the risk of infection of the wound. To that end, various types of antimicrobial dressings have been developed. Examples of antimicrobial agents that have been explored for use in wound dressings include conventional antiseptics, antibiotics, antimicrobial peptides, or metallic agents with antimicrobial properties. For example, silver-containing compounds, such as silver salts, are commonly used in antimicrobial wound dressings.

WO2008057155 discloses silicone gel forming compositions for temporarily adhering a medical device to a biological substrate, such as skin. Said disclosure teaches silicone gel compositions comprising active agents, for instance antibiotics, antiseptics, antifungals, anti-inflammatory agents, hormones, anticancer agents, histamine blockers, beta blockers, vitamins, sedatives, analgesics, proteolytic enzymes, and peptides, which can be bound in the composition. However, the release of the active agent from the hydrophobic adhesive matrix, i.e. the silicone gel forming composition, is typically limited as active agents are bound in the composition.

WO 2011/129759 discloses an antimicrobial silicone gel adhesive (and wound dressing including a layer of such silicone gel adhesive) comprising at least one silver salt and at least one hydrophilic component, wherein the hydrophilic component facilitates the absorbance of moisture in the adhesive layer and thereby affording an improved release of silver from the adhesive matrix.

However, there is still a need in the art to provide an improved adherent medical dressing.

SUMMARY OF THE INVENTION

In view of the above-mentioned and other drawbacks of the prior art, a general object of the present invention is to provide an adherent medical dressing, in particular to provide an adherent medical dressing capable of achieving an instant and sustained release of a chemical compound, such as an antimicrobial compound, whilst maintaining a presence of a chemical compound in the dressing.

According to a first aspect of the invention, these and other objects are achieved through a medical dressing comprising a substrate comprising a first chemical compound, the substrate having a first surface, wherein the medical dressing further comprises an adhesive layer having a skin-facing surface to adhere the medical dressing to a dermal surface, wherein at least a portion of the skin-facing surface comprises a coating comprising a second chemical compound.

The invention is based on the realization that an improved release of active chemical compound(s) and/or an improved biological activity (e.g. antimicrobial and/or wound healing activity) from an adherent medical dressing can be achieved by combining an inner substrate comprising a first chemical compound, with an adhesive layer having a skin-facing surface comprising a coating comprising a second chemical compound, which coating is intended to be in direct contact with the wound and/or surrounding dermal surface during use. Thereby, the coating on the adhesive layer provides a rapid initial release of the second chemical compound whilst the inner substrate provides a more slow release of the first chemical compound to ensure that the release thereof is maintained over a desirable period of time and/or that a biological (e.g. antimicrobial) activity therefrom is maintained within the inner substrate.

In embodiments of the invention, the first surface of the substrate faces the adhesive layer, and the skin-facing surface of the adhesive layer faces away from the first surface of the substrate.

In embodiments of the invention, the adhesive layer may comprise a silicone based adhesive. The inventors have realized that a silicone based adhesive is particular suitable as chemical compounds can be included in a coating thereon without substantially affecting the adhesive properties of the adhesive layer whilst the chemical compounds can be readily released therefrom.

The term "coating" should, in the context of this application, be understood as at least one continuous layer on a surface, or a plurality of dots or layers, or a discontinuous cover on a surface e.g. plurality of particles distributed on an area of a surface.

In embodiments of the invention, the coating comprising the second chemical compound on at least a portion of the skin-facing surface of the adhesive layer may comprise a plurality of particles of the second chemical compound distributed on at least a portion of the skin-facing surface, wherein a first portion of each particle may penetrate into the adhesive layer whilst a second portion of the particle may protrude out from the adhesive layer.

In embodiments of the invention, the coating comprising the second chemical compound on the adhesive layer may, for example, be a film coating comprising a composition of the second chemical compound and a film forming or carrier chemical compound (e.g. a polymeric compound).

In embodiments of the invention, the substrate may comprise an absorbent material. For example, the absorbent material may be a polymeric foam such as a hydrophilic polyurethane foam, a non-woven material, fibrous material such as fibrous hydrophilic polymeric material, gel forming fibers, hydrogel, a matrix containing hydrocolloids, woven and knitted fibers, or combinations thereof. Thereby, the medical dressing is capable of absorbing and retaining exudates from a wound.

As used herein, the term "hydrophilic" refers to the water-permeability property of a material or the water-attracting property of a molecule. In the context of a material with pores (such as, for example, open-cell foams) or materials with through-holes, such a material is "hydrophilic" if the material wicks up water. In the context of a material without pores or any through-holes, such a material is considered "hydrophilic" if it does not resist the flow of water into or through the material. For example, hydrophilicity of a material can be tested using a water column of up to one inch height exerting pressure on the material for at least 60 minutes, at least 90 minutes, or at least 24 hours. By "resisting," it is meant that any flow of water into or through the foam in such a test is below a detection limit for the test.

In embodiments of the invention, the substrate may comprise a layer of hydrophilic polyurethane foam material. For example, the hydrophilic foam may be an open-cell porous foam such as a hydrophilic polyurethane foam. The foam may for example be a polyurethane foam produced from a composition comprising a prepolymer based on: hexamethylene diisocyante (HDI), toluene diisocyanate (TDI), or methylene diphenyl diisocyanate (MDI).

In embodiments of the invention, the adhesive layer may be a coating on at least a portion of the first surface of the substrate, thereby facilitating the application of the dressing to a dermal surface, e.g. a wound site, and securing the substrate of the medical dressing to desired position, for example, such that the substrate adheres to and covers a wound. By providing a coating comprising a second chemical compound, such as for example an antimicrobial compound or wound healing compound, on the skin-facing surface of the adhesive layer, the release of the second chemical compound can be controlled and restricted to a desired application area.

In embodiments of the invention, the medical dressing may further comprise a perforated film layer sandwiched between the first surface of the substrate and the adhesive layer, wherein the adhesive layer is a coating on a non-perforated portion of the perforated film layer. For example, a top surface of a perforated film layer may be attached to first surface of the substrate, wherein the adhesive layer may be coated on a bottom surface of a non-perforated portion of the perforated film, and wherein the top surface of the perforated film layer is opposite to, or faces away from, the bottom surface thereof.

Accordingly, the first surface of the substrate may be exposed through the openings of the perforated film layer, thereby facilitating the absorption of exudates and wound fluids from the wound, and/or facilitating the release of the first chemical compound from the substrate to the wound, through the openings.

By the term "attached" as used herein should be understood one physical element being in contact with another physical element, e.g. a first layer being in contact with an adjacent second layer. For example, in embodiments of the invention, the term "attached" may mean that one layer is adhered or laminated to another layer by means of an adhesive in between the attached layers, alternatively two layers may be "attached" without direct adhesive means therebetween, for example, one layer may be placed on top of another layer wherein the layers are held together by additional surrounding layers enclosing the "attached" layers.

In embodiments of the invention, the first chemical compound may be distributed or incorporated within the substrate.

In embodiments of the invention, the first chemical compound may be a solid dispersion in the substrate. The first chemical compound may be a substantially homogenous solid dispersion in the substrate. For example, the first chemical compound may be a molecular dispersion or partial molecular dispersion in the substrate. By "molecular dispersion" should be understood isolated molecules of the chemical compound, and by "partial molecular dispersion" should be understood a plurality of isolated molecules as well as a plurality of isolated clusters of molecules e.g. crystals or particles.

In embodiments of the invention, the substrate may be impregnated with the first chemical compound. For example, the substrate may be a foam having an open cell structure, wherein the first chemical compound may be present as a coating on the cell walls of the foam. For example, the substrate may be soaked with a solution or dispersion containing the first chemical compound.

In embodiments of the invention, the first surface of the substrate may comprise a coating comprising the first chemical compound. In case the coating is present on a porous material (e.g. foam), the coating may, at least to some extent, penetrate below the general surface face of the material, e.g. the coating may cover at least a portion of the walls in openings or pores in a foam structure. For example, in embodiments of the invention, the first chemical compound may be present only as a coating on the first surface of the substrate, or the first chemical compound may be present both as a coating on the first surface of the substrate and being distributed within the substrate, thereby a gradient of concentration of the first chemical may be achieved, wherein the first chemical compound may be present at a higher concentration on the first surface of the substrate thus further promoting release therefrom, whilst a lower concentration in the bulk of the substrate provides a battery of the first chemical compound that can be slowly released to the wound and/or exert its activity; e.g. antimicrobial activity, within the substrate.

In embodiments of the invention, the substrate may include a plurality of layers of the same or different materials. For example, the substrate may comprise a wound facing layer of absorbent foam material, a middle fibrous gel forming layer, and a top non-woven layer, wherein the middle layer may be sandwiched between the wound facing layer and the top layer. Thereby the liquid absorption properties of the medical dressing may be adapted as desired. Further, the first chemical compound may be incorporated with all or only selected layer of the substrate to achieve a desirable release from and/or activity within the substrate.

In embodiments of the invention, the first chemical compound and/or the second chemical compound may be an antimicrobial compound.

In embodiments of the invention, the medical dressing is an antimicrobial dressing.

In embodiments of the invention, the first chemical compound and the second chemical compound may independently be selected from the group consisting of a silver compound such as silver salt and metallic silver, biguanide salts such as polyhexamethylene biguanide (PHMB) or any salts thereof, or polyhexamethyl guanide (PHMG) or any salts thereof, or chlorhexidine or any salts thereof, iodine, salicylic acid or any salt thereof, acetylsalicylic acid or any salt thereof, quarter ammonium salts such as benzethonium chloride, povidone-iodine (betadine), lactoferrin, xylitol, antimicrobial peptides such as human cationic antimicrobial protein 18 (known as hCAP18 or LL37), borneol, bismuth subgallate, antifungal pharmaceuticals, and antibiotics such as gentamycin, streptomycin.

In embodiments of the invention, the first chemical compound and the second chemical compound may independently be selected from the group consisting of a silver compound including e.g. a silver salt and metallic silver; biguanide salts such as PHMB or any salts thereof, or PHMG or any salts thereof; chlorhexidine or any salts thereof; and iodine.

For example, the first chemical compound and/or the second chemical compound may be a silver salt such as silver sulfate ($Ag_2SO_4$), silver sulfite ($Ag_2SO_3$), silver nitrate ($AgNO_3$), silver carbonate ($AgCO_3$), silver phosphate ($Ag_3PO_4$), silver chloride (AgCl), silver sodium hydrogen zirconium phosphate (AlphaSan® from Milliken Chemical, Spartanburg, USA), or PHMB e.g. PHMB hydrochloride or any other salts thereof, or chlorhexidine or any salts thereof.

For example, the first chemical compound and/or the second chemical compound may be a silver compound, for example a silver salt or metallic silver.

In embodiments of the invention, the first chemical compound may be present in a first concentration by area of the medical dressing and the second chemical compound may be present in a second concentration by area of the medical dressing, wherein the first and second concentrations may be different. For example, the concentration of the first chemical compound may be about 5 to 3000 $\mu g/cm^2$, and wherein the concentration of the second chemical compound may be about 1 to 2500 $\mu g/cm^2$. By varying the concentrations of the first and second chemical compounds, the release profile of the dressing can be tailor-made for different applications; i.e. different types of wounds.

In embodiments of the invention, the first chemical compound may be present in a first concentration by area of the medical dressing and the second chemical compound may be present in a second concentration by area of the medical dressing, wherein said first concentration may be higher than said second concentration.

As used herein, the terms "about" or "approximately," refer to, for example, a number or percentage, generally including numbers that fall within a range of 5%, 10%, or 20% in either direction (plus or minus) of the number unless otherwise stated or otherwise evident from the context (except where such a number would be physically impossible, e.g. exceed 100% of a possible value or fall below 0% of a possible value).

In embodiments of the invention, the adhesive layer may comprise a third chemical compound incorporated within the adhesive layer, wherein the third chemical compound may be the same as the first and/or second chemical compound. For example, the third chemical compound may be a solid dispersion in the adhesive layer.

In embodiments of the invention, the medical dressing may include a vapor permeable transmission layer attached to the substrate on a second surface thereof, the second surface being opposite to the first surface of the substrate. The transmission layer may typically be water impermeable.

According to a second aspect of the invention, these and other objects are achieved by a method of manufacturing a medical dressing comprising the steps of: providing a substrate comprising a first chemical compound; providing an adhesive layer; and providing a coating comprising a second chemical compound on the adhesive layer. In embodiments of the invention, the adhesive layer may comprise a silicone based adhesive.

According to a third aspect of the invention, the above-mentioned and other objects are achieved through a medical dressing manufactured according to the above-described method.

According to a forth aspect of the invention, the above-mentioned and other objects are achieved through the use of the medical dressing according to the invention for treating and/or preventing wounds. For example, the medical dressing according to the invention may be used in the treatment of burns, scars, bacterial infections, viral infections, fungal infection, and/or for wound healing.

According to a fifth aspect of the invention, the above-mentioned and other objects are achieved through a method of treating a wound comprising the step of providing the medical dressing according to the invention on a wound and/or surrounding dermal surface.

BRIEF DESCRIPTION OF THE DRAWINGS

These and other aspects of the invention will now be shown in more detail, with reference to the appended drawings showing an exemplary embodiment of the invention, wherein:

FIG. 1a is a schematic perspective view of an embodiment of a medical dressing according to the invention;

FIG. 1b is a cross-sectional view along the line A-A in FIG. 1a;

FIG. 2b is a cross-sectional view along the line A'-A' in FIG. 2a;

DESCRIPTION OF EXAMPLE EMBODIMENTS OF THE INVENTION

In the following description, example embodiments of the present invention are described with reference to the accompanying schematic drawings.

Figures 1A, 1B:
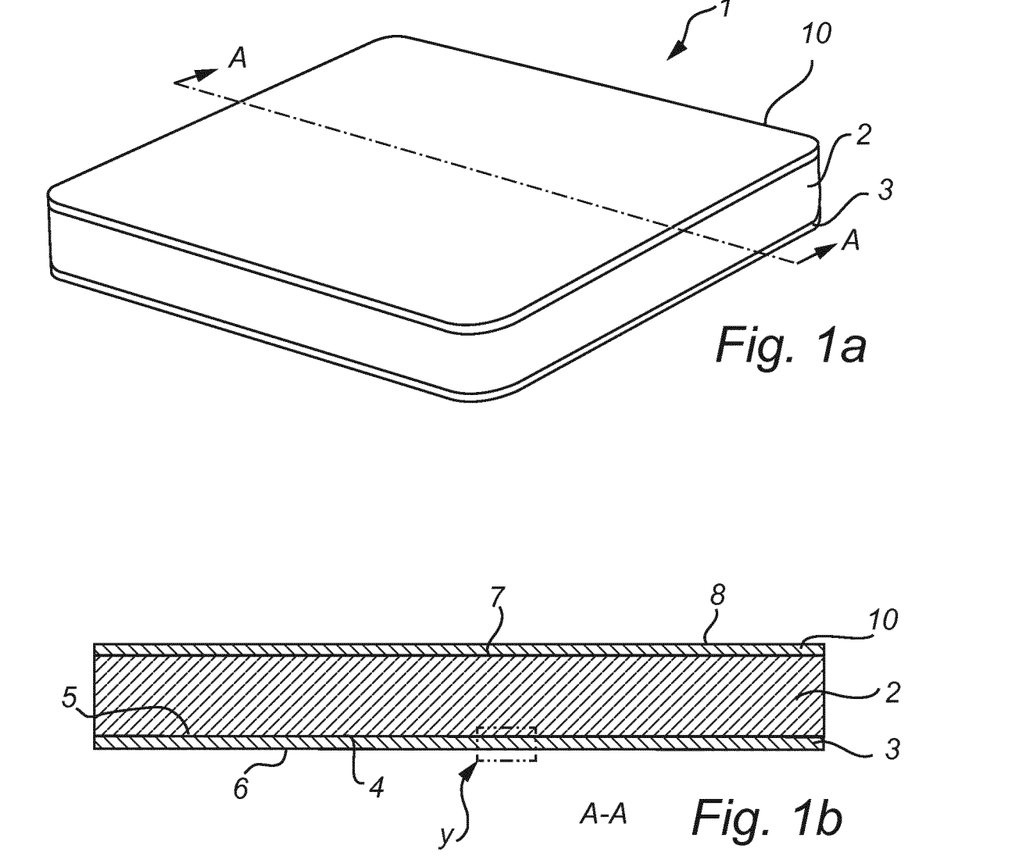
Figure 1C:
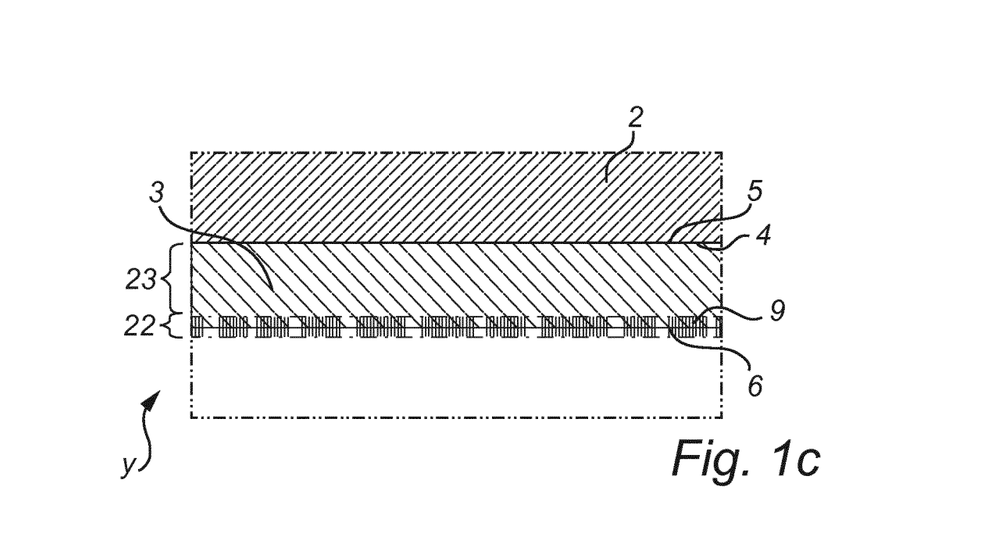
FIG. 1c is an enlarged cross-sectional view of the of the cut out Y in FIG. 1b.

FIGS. 1a-c illustrate an exemplary embodiment of a medical dressing 1 according to the invention. The medical dressing 1 comprises a substrate 2 which comprises a first chemical compound, wherein the medical dressing 1 further comprises an adhesive layer 3 having a skin-facing surface 6 to adhere the medical dressing 1 to a dermal surface (when the medical dressing is in use), and wherein at least a portion of the skin-facing surface 6 comprises a coating 9 comprising a second chemical compound. In the embodiment shown in FIGS. 1a-c, the adhesive layer 3 is a coating on a first surface 4 of the substrate 2, wherein the skin-facing surface 6 of the adhesive layer 3 faces away from the first surface 4 of the substrate 2. The medical dressing of FIGS. 1a-c further comprises a vapor permeable transmission layer 10, wherein the vapor permeable transmission layer 10 overlays a second surface 7 of the substrate 2, which second surface 7 is opposite to the first surface 4 of the substrate 2. The vapor permeable transmission layer 10 may, for example, be attached to the second surface 7 by means of a continuous or discontinous glue layer (e.g. acrylic based adhesive), or by heat lamination.

Figure 2A:
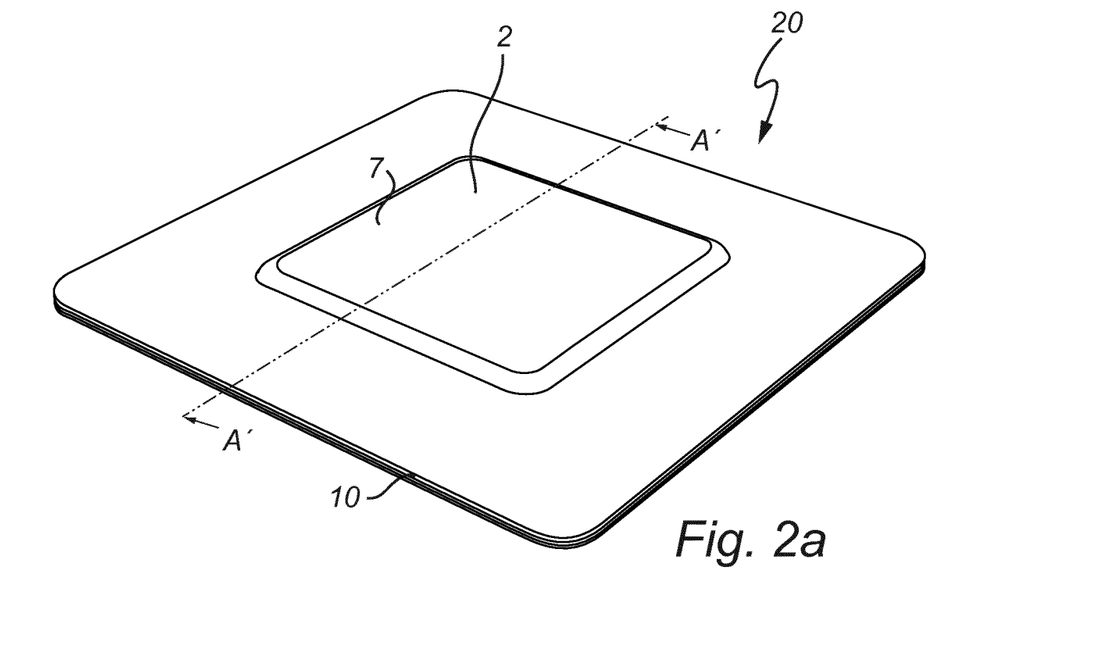
FIG. 2a is a schematic perspective view of an embodiment of a medical dressing according to the invention.
Figure 2B:
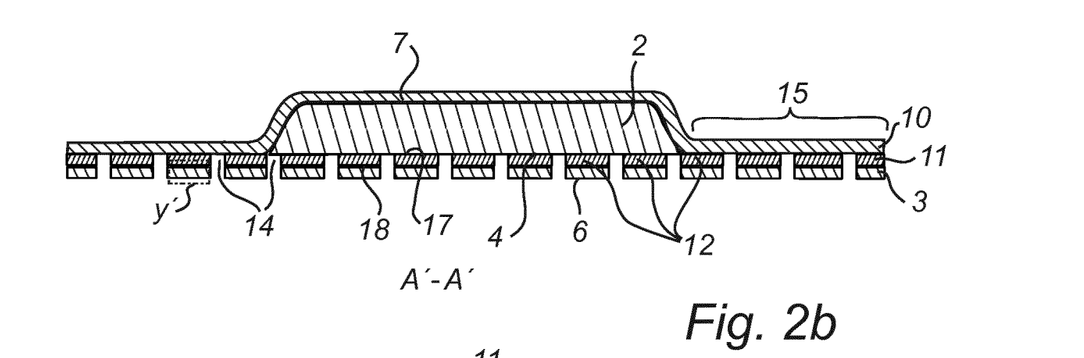
Figure 2C:
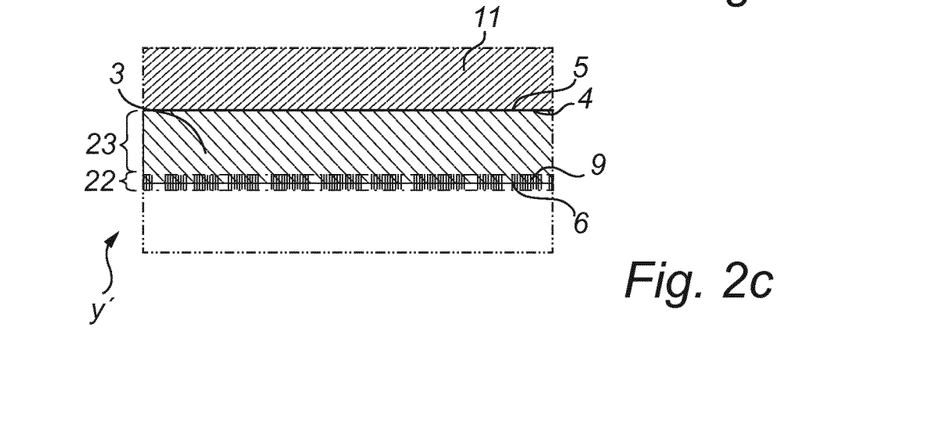
FIG. 2c is an enlarged cross-sectional view of the of the cut out Y' in FIG. 2b.

FIGS. 2a-c illustrate an exemplary embodiment of a medical dressing 20 according to the invention. The medical dressing 20 comprises a substrate 2 which comprises a first chemical compound, wherein the medical dressing 20 further comprises a perforated film layer 11 sandwiched between the first surface 4 of the substrate 2 and the adhesive layer 3, and wherein the adhesive layer 3 is a coating on a non-perforated portion 12 of the perforated film layer 11. As shown in FIG. 2b, a top surface 17 of the perforated film layer 11 may be attached to first surface 4 of the substrate 2, wherein the adhesive layer 3 is coated on a bottom surface 18 of a non-perforated portion 12 of the perforated film layer 11, and wherein the top 17 and bottom 18 surfaces are opposite relative to one another. Accordingly, the first surface 4 of the substrate 2 can be exposed through the openings 14 of the perforated film layer 11, thereby facilitating the absorption of exudates and wound fluids from the wound, and/or facilitating the release of the first chemical compound from the substrate 2 to the wound, through the openings 14.

Further, at least a portion of a skin-facing layer 6 of the adhesive layer 3 comprises a coating 9 comprising a second chemical compound, which coating 9 is intended to be in direct contact with the wound and/or surrounding dermal surface when the medical dressing is in use. Thereby, a rapid release of the second chemical compound to a dermal surface (when dressing is being used) is facilitated, whilst at the same time maintaining the adhesive properties of the adhesive layer 3.

The medical dressing 20, as exemplified in FIGS. 2-c, may further include a vapor permeable transmission layer 10 that overlays a second surface 7 of the substrate 2. The permeable transmission layer 10 may be a plastic film, for example, comprising or consisting of polyurethane, polyethylene, or polypropylene. The vapor permeable transmission layer 10 may be a polyurethane film having a thickness in the range of 10-100 µm, for example, 10-80 µm such as 10-50 µm.

In the embodiment shown in FIGS. 2a-b, both the perforated layer 11 and the vapor permeable transmission layer 10 extend outside the periphery of the substrate 2, and the respective portions of the perforated layer 11 and the vapor permeable transmission layer 10 extending outside the substrate is attached to each other, thereby forming a border portion 15 surrounding the substrate 2. The perforated layer 11 may be attached to the first surface 4 of the substrate 2 and/or to the vapor permeable transmission layer 10 by means of a continuous or discontinuous glue layer (not shown in FIGS. 2a-b).

For example, in one embodiment of the invention, the perforated layer 11 outside the periphery of the substrate 2 is attached to the vapor permeable transmission layer 10 (using e.g. a acrylic based adhesive) whereas the perforated layer 11 facing the first surface 4 of the substrate 2 is not laminated (by means of e.g. glue or heat) to the first surface 4, thus the substrate 2 may be movable in relation to the perforated layer 11 which may for example be desirable if substrate expands in use. Similarly, in embodiments of the invention, the second surface 7 of the substrate 2 may be movably attached to the vapor permeable transmission layer 10, i.e. the layers are not laminated by means of e.g. glue or heat but rather held together by the surrounding laminated border portion 15.

Furthermore, the perforated layer 11 may comprise a plurality of openings 14 (or through holes) of any desirable size and shape. The shape and size may be adapted to achieve a desirable absorption and/or release of the first chemical compound from the substrate 2. For example, the openings 14 may be circular, straight slits, rectangular or square shaped, among others. In embodiments of the invention, the size and/or shape of the openings 14 in the perforated layer 11 are different. For example, in embodiments of the invention, the portion of the perforated layer 11 extending outside the periphery of the substrate 2, in the border portion 15 of the dressing 20, may comprise less number of openings or smaller openings (not shown), or be a continuous film with no openings (not shown), thereby increasing the surface area of the non-perforated portion 12 of the perforated layer 11 in the border portion 15, and thereby increasing stay on ability of the medical dressing 20 as the total area of adhesive layer 3 on the non-perforated potion 12 increases accordingly.

In embodiments of the invention, the perforated layer may comprise an opening substantially corresponding to the area of the first surface of the substrate, wherein the perforated layer is positioned such that the first surface of the substrate coincide with the opening in the perforated layer, thereby substantially all of the first surface of the substrate may be in contact with the wound when the medical dressing is in use (embodiment not shown in Figures).

In embodiments of the invention, the perforated layer 11 may be a plastic film having a thickness of in the range of 10-150 µm. For example, the perforated film 11 may be of polyurethane, polypropylene, or polyethylene.

In embodiments of the invention, the perforated layer 11 may be a polyurethane film having a thickness in the range of 10-150 µm, for example, 10-100 µm or 10-80 µm such as 10-50 µm, for example 25 µm.

In embodiments of the invention, the adhesive layer may be arranged adjacent to a peripheral portion of the substrate, whereby the adhesive layer extends away from the peripheral portion of the substrate. For example, the medical dressing may be an island dressing wherein the adhesive layer surrounds the peripheral portion of the substrate.

For example, in embodiments of the invention, the medical dressing may comprise a vapor permeable transmission layer that overlays a second surface of the substrate, and furthermore extends outside a peripheral portion of the substrate to define a border portion of the vapor permeable transmission layer. In these embodiments of the invention, the adhesive layer may be a coating on a skin-facing border portion of the vapor permeable transmission layer (embodiment not shown in Figures).

In embodiments of the invention, the substrate 2 may typically comprise an absorbent material. For example, such absorbent material may be selected from the group consisting of a polymeric foam such as a hydrophilic polyurethane foam, a non-woven material, fibrous material such as fibrous hydrophilic polymeric material, gel forming fibers, hydrogel, a matrix containing hydrocolloids, woven and knitted fibers.

In embodiments of the invention, the substrate 2 may comprise a layer of a hydrophilic polyurethane foam, for example, a polyurethane foam produced from a composition comprising a prepolymer based on: hexamethylene diisocyante (HDI), toluene diisocyanate (TDI), or methylene diphenyl diisocyanate (MDI).

For example, in embodiments of the invention, the substrate 2 may be a hydrophilic polyurethane foam.

In embodiments of the invention, the first chemical compound may be distributed within the substrate 2. For example, the first chemical compound may be substantially homogenously distributed within the substrate 2, i.e. having a uniform material composition throughout the substrate 2. For example, the first chemical compound may be a substantially homogenous solid dispersion, such as a molecular dispersion or partial molecular dispersion, in the substrate 2.

In embodiments of the invention, the first chemical compound may be chemically bound to the structure or internal surface (e.g. pores) of the substrate 2. For example, in case the first chemical compound is an ionic salt, the first chemical compound may be bound to a charged internal surface of the substrate 2. For example, the substrate may comprise cellulose fibres having a charged side group, such as for example carboxymethyl cellulose (CMC), wherein the first chemical compound may be bound to the cellulose fibres by ionic bonds.

In embodiments of the invention, the first chemical compound may be incorporated into the substrate by including the first chemical in the manufacturing of the substrate. For example, the substrate may be a foam, wherein the first chemical compound is added to the pre-polymer before the foaming step (e.g. according to the method disclosed in EP 1 964 580), thereby the first chemical compound may be incorporated within the structure of the substrate, e.g. chemically bounded within the cell walls of a foam substrate.

In embodiments of the invention, the first chemical compound may be impregnated in the substrate 2, for example, the first chemical compound may be a coating on the internal surface of the substrate 2. For example, in case the substrate is a foam substrate, the first chemical compound may be a coating on the internal pore surfaces of the foam.

In embodiments of the invention, the first surface 4 of the substrate 2 may comprise a coating comprising the first chemical compound.

In embodiments of the invention, the first surface 4 of the substrate 2 may comprise a coating comprising the first chemical compound, wherein said coating may also comprise a carrier or film forming chemical compound. For example, the carrier or film forming chemical compound may be polymeric material such as polyvinylpyrrolidone (PVP), carboxymethyl cellulose (CMC), hydroxyethyl cellulose (HEC), polyvinyl alcohol (PVA), and/or hydroxypropyl cellulose (HPC). The carrier or film forming chemical compound may be used to further adapt and control the release of the first chemical compound.

In embodiments of the invention, the first chemical compound may be a substantially homogenous solid dispersion within the core of the substrate 2, and wherein the first surface 4 of the substrate 2 may comprise a coating comprising the first chemical compound. Thus, different concentrations of the first chemical within the substrate may be achieved, and thereby the release and/or activity of the first chemical compound may be adapted as desired. For example, by adding a coating of the first chemical compound to the first surface 4 of the substrate 2, in which substrate the first chemical compound is already distributed, a first concentration of the first chemical compound may be achieved at the first surface 4 and a second concentration of the first chemical compound may be achieved within the core of the substrate 2, thereby the release of the first compound from the substrate 2 may be controlled by adapting the first concentration and the activity (e.g. antimicrobial activity) of the first chemical compound within the substrate may be ensured by adapting the second concentration.

In embodiments of the invention, the coating comprising the second chemical compound may be in the form of particles (e.g. crystals or precipitate) wherein at least a portion of each particle 9 penetrates into the adhesive layer 3, whilst a second portion of the particle protrudes up from the adhesive layer 3 above the skin-facing surface 6 thereof. Thus, as the coating comprising the second chemical compound is on and/or protruding up from the adhesive layer 3, the release of the second chemical compound from the skin-facing surface 6 of the adhesive layer 3 is facilitated.

In embodiments of the invention, as illustrated in FIG. 1c, the adhesive layer 3 may comprise a skin portion 22 including the adhesive material of the adhesive layer 3 proximal to the skin-facing surface 6, and a non-skin portion 23 including the adhesive material proximal to the non-skin facing surface 5 of the adhesive layer 3 being opposite to the skin-facing surface 4, wherein the substrate portion 23 is substantially free from the second chemical compound.

In embodiments of the invention, the coating 9 comprising the second chemical compound on the skin-facing surface 6 of the adhesive layer 3 may be a film coating further comprising a film forming or carrier chemical compound such as, for example PVP, CMC, HEC, PVA, and/or HPC. For example, in such film coating the second chemical compound may be enclosed in a matrix of the film forming or carrier chemical compound. Thereby, the release of the second chemical compound may be further controlled by selecting a film forming or carrier chemical compound having desirable properties, that is, by selecting for example a film forming or carrier chemical compound that has more or less solubility in an aqueous solution (e.g. wound fluid) the release of the second chemical can be adapted as desired.

In embodiments of the invention, the adhesive layer 3 may comprise a silicone based adhesive, acrylic adhesive, or a pressure-sensitive adhesive (PSA) hotmelt.

In embodiments of the invention, the adhesive layer 3 may be a coating having a coating weight of from 20 to 300 $g/m^2$, for example from 50 to 200 $g/m^2$ such as from 80 to 150 $g/m^2$.

In embodiments of the invention, the adhesive layer 3 may be a silicone based adhesive. For example, the silicone based adhesive may be a soft silicone gel adhesive which adhesive is known for its advantageous skin friendly properties as inter alia no or little skin is stripped off when an adhesive layer of soft silicone gel adhesive is removed from a dermal surface. The term "silicone gel" refers to a silicone gel that comprises a cross-linked network including silicone of lower molecular weight. For example, suitable soft silicone gel adhesives can be composed of an addition-cured RTV (Room Temperature Vulcanizing) silicone system which, after admixture, crosslinks and forms a self-adhesive elastomer. One example of a commercially available RTV addition-cured silicone system is Wacker SilGel 612 which is a two-component system, wherein the softness and degree of adherence of the formed elastomer can be varied by varying the proportions of the two components A:B from 1.0:0.7 to 1.0:1.3. Other examples of silicone based adhesives include inter alia NuSil MED-6340, NuSil MED3-6300 and NuSil MED 12-6300 from NuSil Technology, Carpinteria, Ga., USA, and Dow Corning 7-9800 from Dow Corning Corporation, Midland, USA. In embodiments of the invention, the first chemical compound and the second chemical compound may independently be selected from the group consisting of a silver compound including e.g. a silver salt and metallic silver, biguanide salts such as polyhexamethylene biguanide (PHMB) or any salts thereof, or polyhexamethyl guanide (PHMG) or any salts thereof, or chlorhexidine or any salts thereof, iodine, salicylic acid or any salt thereof, acetylsalicylic acid or any salt thereof, quarter ammonium salts such as benzethonium chloride, povidone-iodine (betadine), lactoferrin, xylitol, antimicrobial peptides such as LL37 peptides, borneol, bismuth subgallate, antifungal pharmaceuticals, and antibiotics such as gentamycin, streptomycin.

In embodiments of the invention, the first chemical compound and the second chemical compound may independently be selected from the group consisting of a silver compound including e.g. a silver salt and metallic silver; PHMB or any salts thereof; PHMG or any salts thereof; chlorhexidine or any salts thereof; and iodine.

For example, the first chemical compound and/or the second chemical compound may be a silver salt such as silver sulfate ($Ag_2SO_4$), silver sulfite ($Ag_2SO_3$), silver nitrate ($AgNO_3$), silver carbonate ($AgCO_3$), silver phosphate ($Ag_3PO_4$), silver chloride ($AgCl$), silver sodium hydrogen zirconium phosphate (AlphaSan® from Milliken Chemical, Spartanburg, USA), or PHMB e.g. PHMB hydrochloride or any other salts thereof, or chlorhexidine or any salts thereof.

For example, in embodiments of the invention, the first chemical compound may be a silver compound e.g. silver salt or metallic silver, wherein the second chemical compound may be PHMB or any salts thereof. Alternatively, the first chemical compound may be PHMB or any salt thereof and second compound may be a silver compound or both the first and second may be PHMB or any salt thereof, or both the first and second may be a silver compound. Alternatively, chlorhexidine or any salts thereof may be combined with a silver compound.

In embodiments of the invention, the first chemical compound may be present in a first concentration by area of the medical dressing and the second chemical compound may be present in a second concentration by area of the medical dressing, wherein the first and second concentrations may be different. For example, said first concentration may typically be higher than said second concentration.

In embodiments of the invention, the concentration of the first chemical compound may be about 5 to 3000 $\mu g/cm^2$, and wherein the concentration of the second chemical compound may be about 1 to 2500 $\mu g/cm^2$. For example, the concentration of the first chemical compound may be about 50 to 2000 $\mu g/cm^2$, and wherein the concentration of the second chemical compound may be about 1 to 150 $\mu g/cm^2$. For example, the concentration of the first chemical compound may be about 1000 to 2500 $\mu g/cm^2$, and wherein the concentration of the second chemical compound may be about 1 to 300 $\mu g/cm^2$. For example, the concentration of the first chemical compound may be about 1500 to 2000 $\mu g/cm^2$, and wherein the concentration of the second chemical compound may be about 1 to 100 $\mu g/cm^2$. For example, the concentration of the first chemical compound may be about 50 to 200 $\mu g/cm^2$ such as 95 $\mu g/cm^2$, and wherein the concentration of the second chemical compound may be about 5 to 49 $\mu g/cm^2$ such as 20 $\mu g/cm^2$.

For most wound care applications, it is desirable to incorporate a larger amount of the first chemical compound into the substrate, and a smaller amount of the second chemical compound in the surface coating.

For example, the ratio between the second and the first concentration may be in the range of 1:5 to 1:100, e.g. 1:10 to 1:50.

This allows for both a strong initial, and sustained effect of the first and second chemical compounds. The release of the first and second chemical compounds can be maintained over a desirable period of time and the biological activity of the chemical compounds can be maintained over a desirable period of time.

Different types of wounds pose different demands on a dressing. For application on deep wounds, resulting from e.g. surgery, it may be advantageous to provide a more prominent initial release of the second chemical compound to facilitate early healing and avoid swelling at the wound site. For the purposes of infection prevention or remediation of scars, a slower release may be desired.

By varying the concentrations of the first and second chemical compounds, the release profile of the dressing can be tailor-made for different applications. This allows for a more controlled release of the first and second chemical compounds.

A dressing according to the invention allows for a synergistic effect by providing a rapid initial release of the second chemical compound, whilst a more slow release of the first chemical compound from within the substrate. This allows for a more controlled release profile, and thereby a strong initial, effect as well as sustained effect.

In embodiments of the invention, the first chemical compound and/or the second chemical compound may be a wound healing compound, wherein the first chemical compound and/or the second chemical compound may independently be selected from the group consisting of Edaravone (3-methyl-1-phenyl-2-pyrazolin-5-one); full protein or peptides of: amelogenin, fibronectin, vitronectin, fibrinogen; arginylglycylaspartic acid (RGD) peptides; betaglucan (BG) (e.g. soluble BG or oat BG), growth factors such as platelet-derived growth factor (PDGF), epidermal growth factor (EGF), fibroblast growth factor (FGF); cytokines such as transforming growth factor (TGF) beta 1, TGF beta 3, interleukin (IL)-10; decellularized animal tissue; and amniotic tissue.

In embodiments of the invention, the first chemical compound may be an antimicrobial compound selected from the group consisting of silver compound including e.g. a silver salt and metallic silver; PHMB or any salts thereof; PHMG or any salts thereof, chlorhexidine or any salts thereof; and iodine, wherein the second chemical compound may be a wound healing compound selected from the group consisting of Edaravone (3-methyl-1-phenyl-2-pyrazolin-5-one); full protein or peptides of: amelogenin, fibronectin, vitronectin, fibrinogen; arginylglycylaspartic acid (RGD) peptides; betaglucan (BG) (e.g. soluble BG or oat BG), growth factors such as platelet-derived growth factor (PDGF), epidermal growth factor (EGF), fibroblast growth factor (FGF); cytokines such as transforming growth factor (TGF) beta 1, TGF beta 3, interleukin (IL)-10; decellularized animal tissue; and amniotic tissue.

In embodiments of the invention, the adhesive layer 3, as for example discussed above with reference to FIGS. 1a-c and FIGS. 2a-c may comprise a third chemical compound distributed within the adhesive layer 3, wherein the third chemical compound may be same as the first and/or second chemical compound. In embodiments of the invention, the third chemical compound may be a solid dispersion in the adhesive layer 3.

Accordingly, the chemical compounds may be further distributed within or on the layers or materials of the dressing 1, 20, thereby the properties, e.g. release properties and/or biological (e.g. antimicrobial or wound healing) activity, may be further adapted as desired.

The invention also relates to a method of manufacturing a medical dressing comprising the steps of:

providing a substrate 2 comprising a first chemical compound;

providing an adhesive layer 3; and providing a coating 9 comprising a second chemical compound on the adhesive layer 3.

In embodiments of the invention, the step of providing a substrate 2 comprising a first chemical may include impregnating the substrate 2 with a solution or dispersion of the first chemical compound in a solvent and subsequently drying the impregnated substrate 2. Alternatively, or additionally, the step of providing a substrate 2 comprising a first chemical may include adding the first chemical compound to a step of manufacturing of the substrate.

In embodiments of the invention, the step of providing an adhesive layer 3 may include the step of coating an adhesive composition on the first surface 4 of the substrate or on a non-perforated portion 12 of a perforated film layer 11 (e.g. polyurethane film). For example, in case the adhesive layer is a silicone based adhesive, the step of coating is typically followed by a step of curing the silicone composition to achieve a cured silicone based adhesive layer. For example, the step of providing an adhesive layer may include first adding and then curing a silicone composition on a second surface 18 of a non-perforated portion of a perforated polyurethane film, and subsequently attaching the perforated polyurethane film to the substrate such that a first surface 17 of the perforated polyurethane film is facing the first surface 4 of the substrate, and wherein the first surface 17 of the perforated polyurethane film is opposite to the second 18 surface thereof.

In embodiments of the invention, the step of providing the adhesive layer 3 with a coating 9 comprising a second chemical compound may include adding the second chemical compound to the skin-facing surface 6 of the adhesive layer 3 in the form of a solid, e.g. a powder, alternatively, the second chemical compound may be dissolved or dispersed in a suitable solvent, e.g. water or organic solvents such as alcohol, thus a solution or suspension of the second chemical compound may be applied to the adhesive layer 3, in which case the method typically comprise a further step of drying, e.g. evaporating the liquid. In embodiments of the invention, a liquid mixture (e.g. solution or suspension) of the second chemical compound may further comprise a film forming or carrier chemical compound (as discussed above), thereby a film coating comprising the second chemical compound and the film forming chemical compound may be achieved. A liquid mixture (e.g. solution or suspension) of the second chemical compound may be applied by means of, for example, a sponge applicator, a brush, or a stick, or a roller, or by spreading with a spatula, or by release by a release sheet, or the liquid mixture may be in the form of a spray, mousse, aerosol, or foam which may be directly applied to the surface. For example, a liquid mixture (e.g. solution or suspension) of the second chemical compound may typically be applied to the adhesive layer 3 by spraying the liquid mixture on the skin-facing surface 6 of the adhesive layer 3. In embodiments of the invention, in case the second chemical compound is dissolved or dispersed in a solvent, the viscosity of the solvent may be configured to thereby control the level of penetration of the second chemical compound into the skin-facing surface 6 of adhesive layer 3. For example, the viscosity of a liquid mixture (e.g. solution or suspension) of the second chemical compound may typically have a relatively low viscosity, such as for example within the range of 0.65 to 500 mPas.

Where features, embodiments, or aspects of the present invention are described in terms of Markush groups, a person skilled in the art will recognize that the invention is also thereby described in terms of any individual member or subgroup of members of the Markush group. The person skilled in the art will further recognize that the invention is also thereby described in terms of any combination of individual members or subgroups of members of Markush groups.

Additionally, it should be noted that embodiments and features described in the context of one of the aspects and/or embodiments of the present invention also apply mutatis mutandis to all the other aspects and/or embodiments of the invention.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The advantages of the invention have been demonstrated in experiments.

EXAMPLES

Preparation of Example Embodiments of the Invention

Materials Used:

Lyofoam™ Max (batch 603092), which is a hydrophilic polyurethane foam product, commercially available from Mölnlycke Health Care AB. Lyofoam™ Max includes a polyurethane backing film present on one side of the foam layer; Mepore® Film (20×30 cm) commercially available from Mölnlycke Health Care AB. Mepore Film consists of a transparent polyurethane (PU) film (25 µm) coated with a polyacrylic adhesive (with a release layer of clay coated paper thereon) on one side of the PU film and a paper frame of silicone coated paper on the opposite side of the PU film;Wacker SilGel® 612 (batch SR 020539) silicone based adhesive (room temperature vulcanization silicone; two component system) commercially available from Wacker; silver sulfate ($Ag_2SO_4$) commercially available from Alfa Aesar;polyethylene (PE) film (100 µm);polyethylene (PE) coated paper) commercially available from Åkerlund & Rausing Group.

The method of coating silicone adhesive on a foam sample is based on the method disclosed in WO 97/42985 (see e.g. page 9). The method of perforating the polyurethane film is based on the method disclosed in EP 1 960 164.

All steps of preparation disclosed below are performed at room temperature (25 deg. C.) unless otherwise stated.

Example 1

An aqueous solution of silver sulfate (4.1 g/L) was prepared. The solution was subsequently substantially uniformly sprayed (using any suitable coating apparatus or e.g. a spray can) on the foam surface of Lyofoam™ Max (20×15 cm). The total amount sprayed was 28.3 µL/cm$^2$. Subsequently, a polyethylene (PE) film (20×15 cm) was applied to the silver coated surface of the foam such that the entire foam surface was covered with the PE film, and a steel roller was applied onto the PE film to compress the underlying foam and thereby impregnate the body of the foam with the aqueous solution of silver sulfate. The PE film was thereafter removed, and the Lyofoam™ Max product was dried at room temperature for at least 24 hours to afford a silver impregnated Lyofoam™ Max sample comprising about 116 µg/cm$^2$ silver sulfate.

A layer (thickness 0.125 mm) of uncured silicone mixture (Wacker Silgel 612, ratio A:B=1.2:1) was applied to a PE coated paper (25×25 cm). Subsequently, the silver impregnated (about 116 µg/cm$^2$) Lyofoam™ Max sample (20×15 cm) was applied to the layer of uncured silicone mixture, such that the foam side of Lyofoam™ Max is in contact with the uncured silicone mixture, and the layers (i.e. PE coated paper, silicone, foam layer) were then transported through an oven (90 deg. C.). The silicone mixture was cured in its passage through the oven (total curing time ca. 2 min) to give a cured silicone gel layer on the underside of the foam material. The PE coated paper was removed and a PE film (20×15 cm) was added to cover the cured silicone adhesive layer.

EXAMPLE 2

A Lyofoam™ Max product (20×15 cm, not silver impregnated) was coated with a layer of cured silicone gel adhesive as described in Example 1. An aqueous solution of silver sulfate (7.70 g/L) was prepared and subsequently substantially uniformly sprayed (using any suitable coating apparatus or e.g. a spray can) on the cured silicone layer, and the sample was dried at room temperature for at least 24 h. The total amount sprayed was 15.0 µL/cm$^2$ giving a total amount of silver sulfate on the silicone layer of about 116 µg/cm$^2$.

EXAMPLE 3

A foam sample including the layer of cured silicone gel was prepared as described in Example 1, with the exception that an aqueous solution of silver sulfate with concentration of 3.50 g/L was sprayed (total amount 27.3 µL/cm$^2$) on the foam surface to thereby afford a silver impregnated Lyofoam™ Max sample wherein the total amount of silver sulfate contained in the foam body was about 96 µg/cm$^2$.

The cured silicone gel layer was subsequently coated with silver sulfate as described in Example 2 with the exception that an aqueous solution of silver sulfate with concentration of 3.0 g/L was used and the total amount sprayed was 7.5 µL/cm$^2$, giving a total amount of silver sulfate on the silicone layer of about 22 µg/cm$^2$, and thus a total amount of silver sulfate in the final product of about 118 µg/cm$^2$.

Example 4

A sample of Lyofoam™ Max (20×15 cm) was impregnated as described in Example 1, to achieve a silver impregnated Lyofoam™ Max sample comprising about 116 µg/cm$^2$ silver sulfate.

The paper frame on Mepore® Film (20×30 cm) product was removed and a layer (thickness 0.200 mm) of uncured silicone mixture (Wacker Silgel 612, ratio A:B=112:100) was applied to the top (non-adhesive) surface of the polyurethane (PU) film of Mepore® Film (20×30 cm), and subsequently cured in an own (ca. 2 min, 90 deg. C.). A PE film (20×30 cm) was added to cover the cured silicone adhesive layer.

The PU film now having acrylic adhesive (with release layer) on one side and silicone adhesive (with PE film release layer) on the opposite side was then perforated using an ultrasonic device as described in EP 1 960 164 (see [0008]), wherein the laminate of PU film and release layers was passed though the nip of an ultrasonic device, which comprises an ultrasonic horn and a counter-roller provided with a pattern of protuberances (see FIG. 1 in EP 1 960 164). The laminate was inserted through the ultrasonic device such that the PE film faced the counter-roller. The energy emitted from the ultrasonic device was adjusted so that a localized melting of the PU film occurs in the area of each protuberance, thereby perforating the polyurethane film of the laminate such that a plurality of through holes of ca 1.5 mm in diameter were created. The release layer (on the acrylic adhesive layer) was subsequently removed and the perforated film laminate (cut to 20×15 cm) was attached to the foam surface of the prepared Lyofoam™ Max (comprising about 116 µg/cm$^2$ silver sulfate). The total amount of silver sulfate in the final product was thus about 116 µg/cm$^2$.

Example 5

The paper frame on Mepore® Film (20×30 cm) product was removed and a layer (thickness 0.200 mm) of uncured silicone mixture (Wacker Silgel 612, ratio A:B=112:100) was applied to the top (non-adhesive) surface of the polyurethane (PU) film of Mepore® Film (20×30 cm), and subsequently cured in an own (ca. 2 min, 90 deg. C.). An aqueous solution of silver sulfate (7.70 g/L) was prepared and subsequently substantially uniformly sprayed (using any suitable coating apparatus or e.g. a spray can) on the cured silicone layer, and the sample was dried (at 90 deg. C., ca. 2 min). The total amount sprayed was 15.0 µL/cm$^2$ giving a total amount of silver sulfate on the silicone layer of about 116 µg/cm$^2$. A PE film (20×30 cm) was added to cover the cured silicone adhesive layer, and the film laminate was perforated as described in Example 4 above. Subsequently, the release layer (on the acrylic adhesive layer) was removed and the perforated film laminate (cut to 20×15 cm) was attached to the foam surface of a Lyofoam™ Max product (20×15 cm, not silver impregnated). The total amount of silver sulfate in the final product was thus about 116 µg/cm$^2$.

Example 6

A sample of Lyofoam™ Max (20×15 cm) was impregnated as described in Example 1, with the exception that an aqueous solution of silver sulfate with concentration of 3.50 g/L was sprayed (total amount 27.3 µL/cm$^2$) on the foam surface to thereby afford a silver impregnated Lyofoam™ Max sample wherein the total amount of silver sulfate contained in the foam body was about 96 µg/cm$^2$. A perforated film laminate was prepared as described in Example 5, with the exception that an aqueous solution of silver sulfate with concentration of 3.0 g/L was used and the total amount sprayed was 7.5 µL/cm$^2$, giving a total amount of silver sulfate on the silicone layer of about 22 μg/cm², and thus a total amount of silver sulfate in the final product of about 118 μg/cm².

Example 7

The product was prepared according to Example 4, with the exception that a non-silver impregnated Lyofoam™ Max (20×15 cm) was used. The total amount of silver sulfate in the Example 7 product was thus 0 μg/cm².

Antimicrobial Activity Tests

The antimicrobial effect was determined by a direct contact method, modified ISO 20743:2007 (E) Textiles—Determination of antibacterial activity of antibacterial finished products. The ISO method is modified with respect to test medium and test organisms in order to simulate wound like conditions. In principle, an inoculated test medium is added to a piece of material or product, which absorbs the test medium. The inoculated piece is incubated for a specific time before the number of viable test organisms is determined by washing out the reminding test organisms using neutralization buffer. The viable counts are determined in the neutralizing buffer by serial dilution and plating onto agar plates.

Method Description

Antimicrobial effect was determined on Examples 1-3 and Examples 4-6 against *Pseudomonas aeruginosa* ATCC 15442 (*P. aeruginosa*) and *Staphylococcus aureus* ATCC 6538 (*S. aureus*). Lyofoam™ Max (Mölnlycke Health Care, batch 603092) and Example 7 were included as negative control samples. Any release layers present on the adhesive layer of the Examples were removed prior to testing.

Overnight cultures of test organisms (approximate 10⁹ CFU/ml) in Trypticase Soy Broth (TSB; Acumedia) were diluted to approximate 10⁷ CFU/ml using Peptone Water (PW; 0.85% NaCl with 0.1% peptone Peptone Bacteriological Neutralised (Oxoid)), and then further diluted to approximately 5×10⁶ CFU/ml using Simulated Wound Fluid (SWF; Fetal Calf Serum (Hyclone) and PW mixed in proportions 1:1) to create inoculum for test samples.

Test samples including Examples 1-3 and 4-6, and the negative control samples (LyoFoam™ Max and Example 7), were tested in triplicate for each organism. Circular pieces (Ø 31 mm) of the Examples 1-3 and 4-6 and negative control samples were punched under aseptically conditions and placed into separate Petri dishes with the adhesive silicone layer (or foam side of LyoFoam™ Max) facing up. Aliquots of 0.5 ml of the inoculum were added at several points onto the adhesive silicone layer (or foam surface) on each test sample. The Petri dishes containing the test samples were incubated at 35° C.±2° C. for 24 hours.

To determine the start inoculums levels, additional triplicates of negative control samples, i.e. Lyofoam™ Max and Example 7, were inoculated and directly transferred to separate 250 ml snap cap containers containing 100 ml room temperature D/E. The number of viable counts was determined in the D/E by ten-fold serial dilution in PW and plated onto Petrifilm™ Aerobic Count Plates (3M) and incubated for 48 h before counting colonies. Results were expressed as mean of viable counts (log cfu/sample) per negative control sample.

After incubation (at 35° C.±2° C. for 24 hours), the test samples were transferred to separate 250 ml snap cap containers containing 100 ml room temperature Dey-Engley neutralization buffer (D/E, Becton Dickinson). The containers were rigorously shaken for at least 60 seconds to ensure that surviving test organisms were washed off. The number of viable counts was determined in the D/E by ten-fold serial dilution in PW and plated onto Petrifilm™ Aerobic Count Plates (3M) and incubated for 48 h before counting colonies. Results were expressed as mean of viable counts (log cfu/sample) per negative control sample.

Result and Discussion

The silver content in Examples that were prepared and tested for antimicrobial efficacy is presented in Table 1 below. Examples 1 to 3 (as described above) comprise a silicone adhesive coated directly on a first surface of an hydrophilic foam (LyoFoam™ Max), whereas examples 5 to 8 (as described above) comprise a silicone adhesive coated on a perforated plastic film which plastic film is attached to a first surface of the hydrophilic foam.

TABLE 1

| Example | Ag on silicone adhesive surface (μg/cm²) | Ag in foam (μg/cm²) |
| --- | --- | --- |
| 1 | 0 | 116 |
| 2 | 116 | 0 |
| 3 | 22 | 96 |
| 4 | 0 | 116 |
| 5 | 116 | 0 |
| 6 | 22 | 96 |
| 7 | 0 | 0 |

Figure 3A:
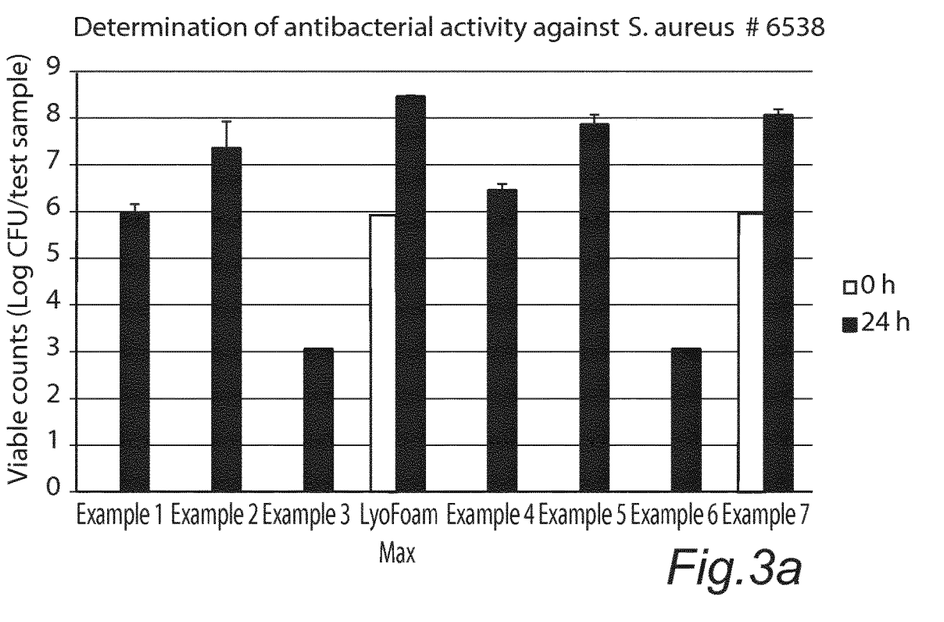
FIGS. 3a-b show the results from an antimicrobial activity test with embodiments of the medical dressing according to the invention.
Figure 3B:
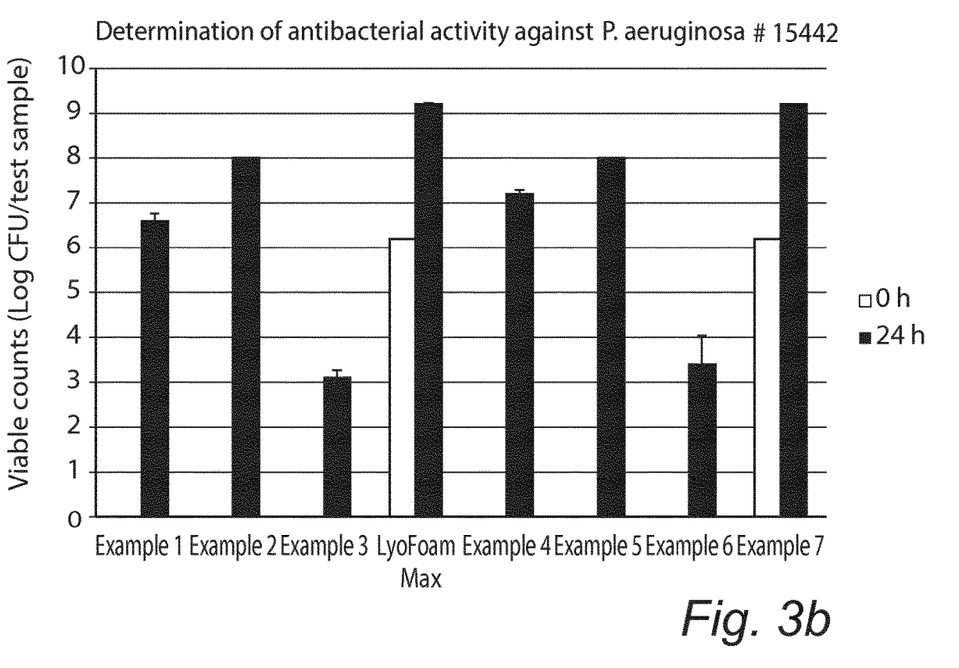

FIG. 3a and FIG. 3b present the result from the antimicrobial activity test against *P. aeruginosa*, and *S. aureus*, respectively. As can be seen in both figures below, the example embodiments according to the invention, i.e. Example 3 and Example 6, both comprising silver salt (Ag₂SO₄) coating on the silicone gel adhesive as well as comprising silver salt in the foam substrate, show a significant reduction of viable counts after 24 h, ca. 3 Log CFU/sample, whereas for the Examples 1, 2, 4, and 5, each having silver salt in only the foam substrate or as a coating on the silicone gel adhesive, show no reduction or even an increase of viable counts after 24 h as compared to the starting inoculums levels measured at 0 h. In fact, these test samples Examples 1, 2, 4, and 5 show similar results as the controls samples Lyofoam™ Max and Example 7 (comprising no silver salt). It should be noted that the total concentration of silver salt in all Examples 1, 2, 3 and 4, 5, and 6, is kept at about the same total level (i.e. 116-118 μg/cm²). Thus, these results are indeed very surprising, and clearly illustrate the technical effect achieved through the invention. Without being bound by theory, it is believed that the significant difference in antimicrobial activity between the inventive Examples 3 and 6, and Examples 1, 2, 4, 5, is due to the fact that the test organisms are in contact with sufficient amounts of silver salt during the testing; irrespective if the test organisms end up on the adhesive silicone gel or in the foam substrate. This is representative for the clinical situation where microorganisms on the surface of the dressing, as well as in the close proximity thereof, will be affected by the silver salt on the adhesive silicone gel, while microorganisms in wound exudates absorbed by the foam substrate will be reduced by the silver salt present therein. It should be further noted that the detection limit of the method is ca. 2.0 Log CFU/test sample. The start inoculums levels (measured at 0 h for the negative control samples only, in accordance with ISO 20743) was 5.9 Log CFU/test sample in the antimicrobial test against *S. aureus* (FIG. 3a) and 6.2 Log CFU/test sample in the antimicrobial test against *P. aeruginosa* (FIG. 3b).

Adhesion Experiments

The purpose of the adhesion experiments was to determine if the adhesive properties of the adhesive silicone layer was affected by a salt coating. To that end, two tests were employed: Adhesive test A (on steel surface) and Adhesive test B (on artificial skin surface). Both tests are based on ASTM D3330/D3330M-04, method F, with the following deviations: (i) resting time after calendering is 30±5 min, whereas in above standard a maximum of 1 minute is used, (ii) mean load measured between 20 and 120 mm, as compared with 25 and 75 mm in above standard; and (iii) for test B roller weight of 445 g, whereas in the above standard the roller weight is 2040 g.

Test A—General test procedure: the steel plate (according to ASTM A 666-94A; PSTC Appendage B 2.6; suitable for slide) was cleaned using a lint-free absorbent material and acetone, and dried at room temperature for 10 min. The cleaning was repeated three times. The adhesive test product (25×220 mm) was applied to the cleaned steel plate without pressing it to the plate. The test piece was calendared (mechanic calender; roller weight 2040±45 g), once back and forth. The sample was rested for 30±5 minutes before testing. A cord was attached from the slide to the crosshead. The cord makes the slide move horizontally at the same speed as the crosshead moves vertically. This ensures that the angle by which the test piece is peeled from the substrate is kept at 90°. The steel plate was put in the slide, and one end of the test product was carefully delaminated from the steel plate and then clamped in the upper clamp together with paper for to avoid slippage. The tensile tester was started, and the mean force required to peel the test piece from the substrate was measured.

Test B—General test procedure: double-coated adhesive tape was applied onto the steel plate (according to ASTM A 666-94A; PSTC Appendage B 2.6) such that no air-bubbles got trapped underneath the tape. The skin substrate (Mitex Membrane 5 µm from Millipore) was applied on the tape carefully to avoid air-bubbles between the skin substrate and the tape (cotton gloves should be worn). The skin substrate was covered to avoid soiling when pressing it to the tape. The adhesive test product (25×220 mm; with a paper strip at the end to avoid soiling of grips) was applied on the substrate, and the specimen was mechanically calendared (roller weight 445 g; or using a manual calender with rubber surface weight 185 g), once back and forth. The sample was left to rest for 30±5 minutes, and subsequently the steel plates was put in the slide and the test product was fasten to the upper grip. A cord was attached from the slide to the crosshead. The tensile tester was started and the mean force required to peel off the silicone strip from the substrate was measured.

Results and Discussion

A number of products were prepared by spraying the silicone adhesive layer of the commercially available products Avance® Film and Mepilex® (from Mölnlycke Health Care) with various amount of sodium chloride (NaCl). The step of spraying a silicone adhesive surface as disclosed above for Example 2 or 5 was employed. Also, Examples 5 and 7 were included in the adhesive test. The results from the adhesion tests (presented in Table 2 below) show that a large amount (e.g. 2500 µg/cm²) can be added without completely lose the adhesive property of the adhesive layer, and for less amount of salt (e.g. up to 1000 µg/cm²) the adhesive properties can be substantially maintained. Thus, the medical dressing according to the invention can indeed be adherent.

TABLE 2

| Product | Test method | Result (N) |
| --- | --- | --- |
| Example 7 (no salt coating) | Method A | 0.53 |
| Example 5 (silicone adhesive coated with 116 µg/cm² Ag$_2$SO$_4$) | Method A | 0.64 |
| Avance ® Film (Mölnlycke Health Care), no salt coating | Method B | 2.43 |
| Avance ® Film, silicone adhesive coated with 750 µg/cm² NaCl | Method B | 2.05 |
| Avance ® Film, silicone adhesive coated with 1000 µg/cm² NaCl | Method B | 2.03 |
| Avance ® Film, silicone adhesive coated with 1500 µg/cm² NaCl | Method B | 1.76 |
| Avance ® Film, silicone adhesive coated with 2000 µg/cm² NaCl | Method B | 1.57 |
| Avance ® Film, silicone adhesive coated with 2500 µg/cm² NaCl | Method B | 1.39 |
| Mepilex ® (Mölnlycke Health Care), no salt coating | Method B | 0.27 |
| Mepilex ®, silicone adhesive coated with 750 µg/cm² NaCl | Method B | 0.26 |
| Mepilex ®, silicone adhesive coated with 1000 µg/cm² NaCl | Method B | 0.19 |
| Mepilex ®, silicone adhesive coated with 1500 µg/cm² NaCl | Method B | 0.18 |
| Mepilex ®, silicone adhesive coated with 2000 µg/cm² NaCl | Method B | 0.16 |
| Mepilex ®, silicone adhesive coated with 2500 µg/cm² NaCl | Method B | 0.10 |

The invention claimed is:

1. A medical dressing comprising:
   a substrate;
   a silicone based adhesive layer provided as a coating on a first surface of the substrate, the adhesive layer having a skin-facing surface that faces away from the first surface of the substrate and being configured to facilitate application of the medical dressing to a dermal surface and secure the substrate of the medical dressing to a desired position such that the substrate adheres to and covers a wound during use;
   a first antimicrobial chemical compound that is substantially homogeneously distributed within the substrate, wherein the first antimicrobial chemical compound is present in a first concentration by area of said medical dressing; and
   a second antimicrobial chemical compound comprising a plurality of particles consisting of only a silver compound, wherein the plurality of particles are distributed on at least a portion of the skin-facing surface of the adhesive layer such that a first portion of each particle penetrates into the adhesive layer and a second portion of each particle protrudes out from said skin-facing surface of the adhesive layer and is configured to be in direct contact with the wound and/or dermal surface surrounding the wound during use, wherein said second antimicrobial chemical compound is present in a second concentration by area of said medical dressing which is different from the first concentration, wherein the second concentration is a concentration from about 1 to 100 µg/cm².

2. The medical dressing according to claim 1, wherein said substrate comprises an absorbent material.

3. The medical dressing according to claim 2, wherein said absorbent material is selected from the group consisting of a polymeric foam, a non-woven material, a fibrous material, a gel forming fiber, a hydrogel, a matrix containing hydrocolloids, a woven fiber, and a knitted fiber.

4. The medical dressing according to claim 1, wherein said medical dressing further comprises a perforated film layer sandwiched between said first surface of said substrate and said adhesive layer, wherein said adhesive layer is a coating on a non-perforated portion of said perforated film layer.

5. The medical dressing according to claim 1, wherein said medical dressing further comprises a vapor permeable transmission layer, wherein said vapor permeable transmission layer overlays a second surface of said substrate, said second surface being opposite to said first surface of said substrate.

6. The medical dressing according to claim 1, wherein said first antimicrobial chemical compound is selected from the group consisting of a silver compound, a biguanide salt, iodine, salicylic acid or any salt thereof, acetylsalicylic acid or any salt thereof, a quarter ammonium salt, povidone-iodine, lactoferrin, xylitol, an antimicrobial peptide, borneol, bismuth subgallate, an antifungal pharmaceutical, and an antibiotic.

7. The medical dressing according to claim 1, wherein said first antimicrobial chemical compound is present at a concentration from about 5 to 3000 $\mu g/cm^2$.

8. The medical dressing according to claim 1, wherein said adhesive layer comprises a third antimicrobial chemical compound distributed within said adhesive layer, wherein said third antimicrobial chemical compound is the same as said first and/or second antimicrobial chemical compound.

9. The medical dressing according to claim 1, wherein said second antimicrobial chemical compound is present at a concentration from about 5 to 49 $\mu g/cm^2$.

10. The medical dressing according to claim 1, wherein said first antimicrobial chemical compound is present at a concentration from about 50 to 200 $\mu g/cm^2$, and wherein said second antimicrobial chemical compound is present at a concentration from about 5 to 49 $\mu g/cm^2$.

11. The medical dressing according to claim 1, wherein said first antimicrobial chemical compound is present at a concentration from about 50 to 200 $\mu g/cm^2$.

* * * * *